United States Patent
Wrublewski et al.

(10) Patent No.: US 6,193,715 B1
(45) Date of Patent: Feb. 27, 2001

(54) DEVICE FOR CONVERTING A MECHANICAL CUTTING DEVICE TO AN ELECTROSURGICAL CUTTING DEVICE

(75) Inventors: Thomas A. Wrublewski, Sharon; Kevin M. Allaire, Mattapoisett; Kevin P. Lemire, E. Douglas; Paul C. Nardella, Sr., Wareham, all of MA (US)

(73) Assignee: Medical Scientific, Inc., Taunton, MA (US)

( * ) Notice: Subject to any disclaimer, the term of this patent is extended or adjusted under 35 U.S.C. 154(b) by 0 days.

(21) Appl. No.: 09/272,272

(22) Filed: Mar. 19, 1999

(51) Int. Cl.$^7$ ................................................ A61B 18/18
(52) U.S. Cl. ............................ 606/45; 606/49; 606/48; 606/50; 606/170; 606/180; 604/22
(58) Field of Search ........................... 606/160, 171, 606/179, 180, 181, 170, 45–50, 41, 42; 604/21, 22

(56) References Cited

U.S. PATENT DOCUMENTS

| | | | |
|---|---|---|---|
| 2,697,909 | 12/1997 | Eggers et al. | 604/114 |
| 3,945,375 | 3/1976 | Banko | 128/6 |
| 4,016,881 | 4/1977 | Rioux et al. | 128/303.17 |
| 4,532,924 | 8/1985 | Auth et al. | 128/303.17 |
| 4,637,390 | 1/1987 | Sorochenko | 128/303.17 |
| 4,657,017 | 4/1987 | Sorochenko | 128/303.14 |
| 4,674,499 | 6/1987 | Pao | 128/303.14 |

(List continued on next page.)

FOREIGN PATENT DOCUMENTS

| | | | |
|---|---|---|---|
| 0596436 | 11/1992 | (EP) | A61B/17/39 |
| 9417741 | 8/1994 | (WO) | A61B/17/39 |

(List continued on next page.)

*Primary Examiner*—Linda C. M. Dvorak
*Assistant Examiner*—David M. Ruddy
(74) *Attorney, Agent, or Firm*—Nutter, McClennen & Fish, LLP

(57) ABSTRACT

An adapter unit for a mechanical tissue cutting implement such as a shaver, morcellator or the like includes a mounting block from which an electrically insulating sheath extends. The sheath fits over the cannula or shaft of the cutting implement, and is secured in alignment and attached so that the cutting tip, for example, the tool and its window in the cannula tip, are exposed through the sheath. A conductor, which may be a conductive layer, extends along the length of the sheath and is exposed to form a distal electrode at the tip in close proximity to the opening, constituting one electrode of a bipolar electrode arrangement at the exposed tool. The other electrode is provided by electrical connection to the implement itself, so that a high current density path is formed through tissue in the cutting region. Preferably both output connections of an electrosurgical generator are coupled through a matching transformer to the mounting block by a plug, socket, cable or fixed cord arrangement, and the mounting block may, for example, be formed of plastic, preferably having an alignment feature such as a notch to fasten to the implement so that the sheath opening aligns with the cutter. Electrical connection to the implement may be effected via a conductive bushing, fastening bolt or the like which contacts one of the supply leads through a wire, spring or other conductive path. The adapter may also provide a sheath opening and distal electrode about a non-apertured region of the cannula, for example on the rear surface of the cannula opposed to the cutting tool aperture, to form a hemostasis element that may be rotated into position to coagulate bleeding. In this case the bipolar electrode geometry may be configured for high energy density delivery that does not vary with tool rotation. The adapter may also convert a monopolar device to bipolar operation, providing a single additional electrode positioned by the sheath at the cutting aperture.

23 Claims, 4 Drawing Sheets

U.S. PATENT DOCUMENTS

| | | | |
|---|---|---|---|
| 4,802,476 | 2/1989 | Noerenberg et al. | 128/303.14 |
| 4,815,462 | 3/1989 | Clark | 128/305 |
| 4,842,578 | 6/1989 | Johnson et al. | 604/22 |
| 4,917,082 | 4/1990 | Grossi et al. | 606/46 |
| 5,037,379 | 8/1991 | Clayman et al. | 600/37 |
| 5,047,027 | 9/1991 | Rydell | 606/48 |
| 5,080,660 | 1/1992 | Buelna | 606/45 |
| 5,085,659 | 2/1992 | Rydell | 606/47 |
| 5,122,138 | 6/1992 | Manwaring | 606/46 |
| 5,133,713 * | 7/1992 | Huang et al. | 606/46 |
| 5,171,255 | 12/1992 | Rydell | 606/170 |
| 5,176,677 | 1/1993 | Wuchinich | 606/46 |
| 5,192,280 | 3/1993 | Parins | 606/48 |
| 5,201,731 | 4/1993 | Hakky | 606/15 |
| 5,217,458 | 6/1993 | Parins | 606/48 |
| 5,217,478 | 6/1993 | Rexroth | 606/180 |
| 5,269,780 | 12/1993 | Roos | 606/42 |
| 5,269,782 | 12/1993 | Sutter | 606/48 |
| 5,269,794 | 12/1993 | Rexroth | 606/180 |
| 5,282,799 | 2/1994 | Rydell | 606/48 |
| 5,290,282 | 3/1994 | Casscells | 606/29 |
| 5,290,303 | 3/1994 | Pingleton et al. | 606/170 |
| 5,297,964 | 3/1993 | Parins | 606/48 |
| 5,304,124 | 4/1994 | Essig et al. | 604/55 |
| 5,318,564 | 6/1994 | Eggers | 606/47 |
| 5,318,589 | 6/1994 | Lichtman | 606/205 |
| 5,330,471 | 7/1994 | Eggers | 606/48 |
| 5,364,395 * | 11/1994 | West, Jr. | 606/46 |
| 5,391,166 | 2/1995 | Eggers | 606/48 |
| 5,403,312 | 4/1995 | Yates et al. | 606/50 |
| 5,411,514 | 5/1995 | Jalbert et al. | 606/48 |
| 5,423,844 | 6/1995 | Miller | 606/171 |
| 5,441,499 | 8/1995 | Fritzsch | 606/45 |
| 5,445,638 | 8/1995 | Rydell et al. | 606/51 |
| 5,456,689 | 10/1995 | Kresch et al. | 606/180 |
| 5,480,397 | 1/1996 | Eggers et al. | 606/29 |
| 5,484,435 | 1/1996 | Fleenor et al. | 606/46 |
| 5,492,527 | 2/1996 | Glowa et al. | 604/22 |
| 5,527,331 | 6/1996 | Kresch et al. | 606/170 |
| 5,531,677 | 7/1996 | Lundquist et al. | 604/22 |
| 5,569,244 | 10/1996 | Hahnen | 606/46 |
| 5,571,100 | 11/1996 | Goble et al. | 606/41 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,810,809 * | 9/1998 | Rydell | 606/49 |
| 5,902,272 * | 5/1999 | Eggers et al. | 604/114 |
| 5,904,681 * | 5/1999 | West, Jr. | 606/41 |
| 5,913,857 * | 6/1999 | Ritchart et al. | 606/45 |
| 5,941,876 * | 8/1999 | Nardella et al. | 606/45 |
| 6,004,320 * | 12/1999 | Casscells et al. | 606/49 |
| 6,032,673 * | 3/2000 | Savage et al. | 128/898 |

FOREIGN PATENT DOCUMENTS

| | | | |
|---|---|---|---|
| 9611638 | 4/1996 | (WO) | A61B/17/32 |
| 9624296 | 8/1996 | (WO) | A61B/17/20 |
| 97/33523 * | 9/1997 | (WO) | 606/45 |
| 9724074 | 10/1997 | (WO) | A61B/17/39 |

* cited by examiner

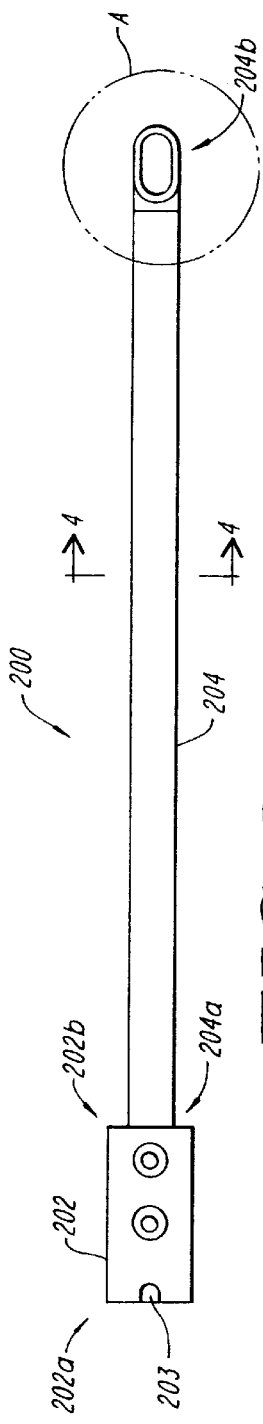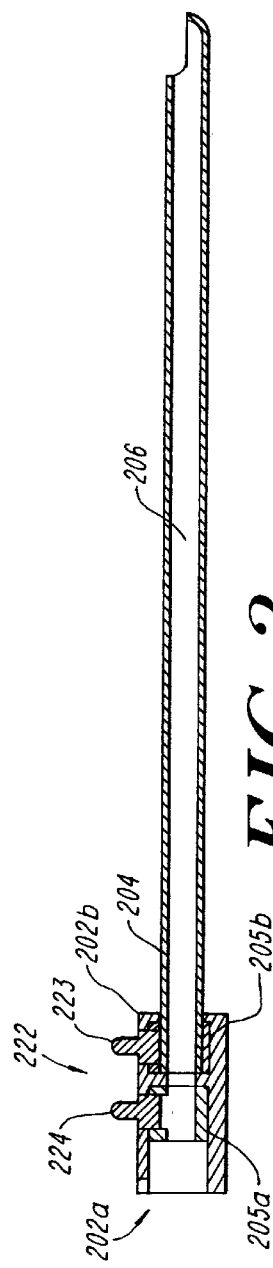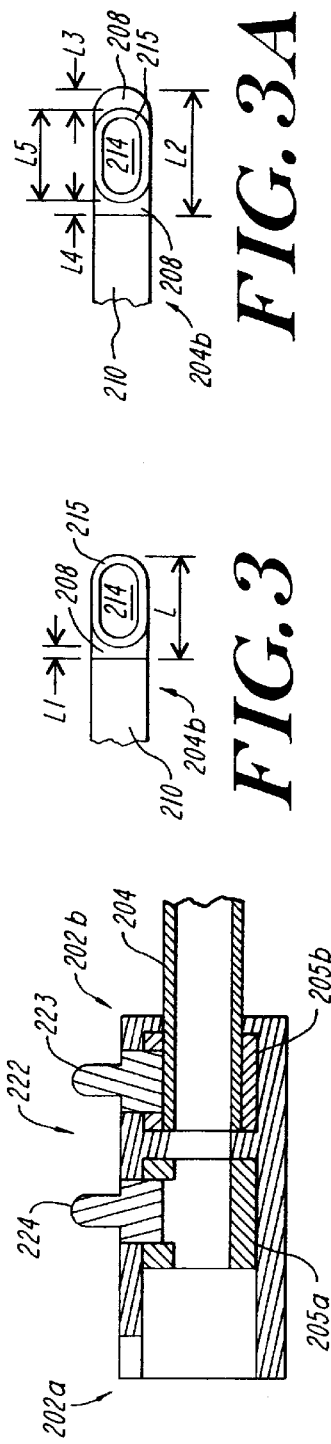

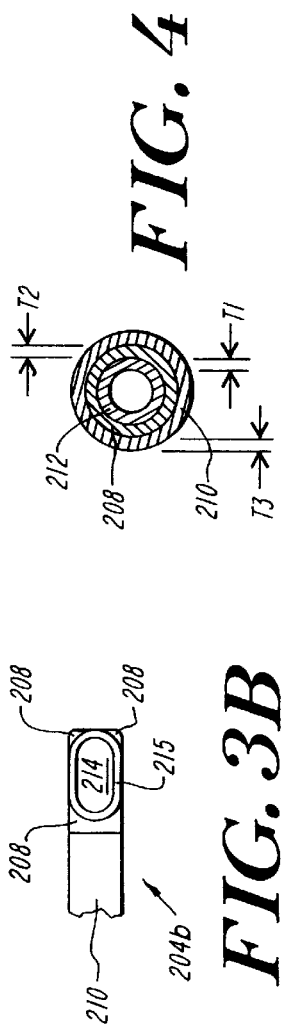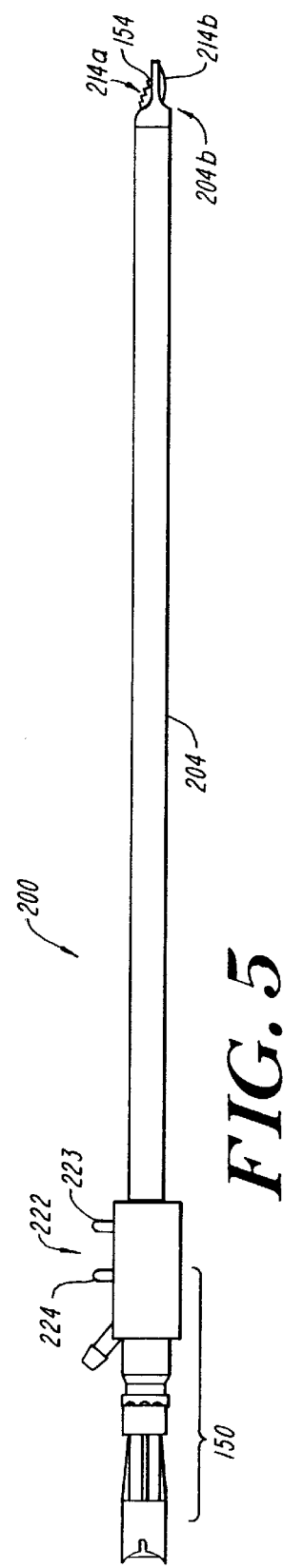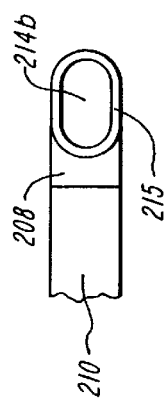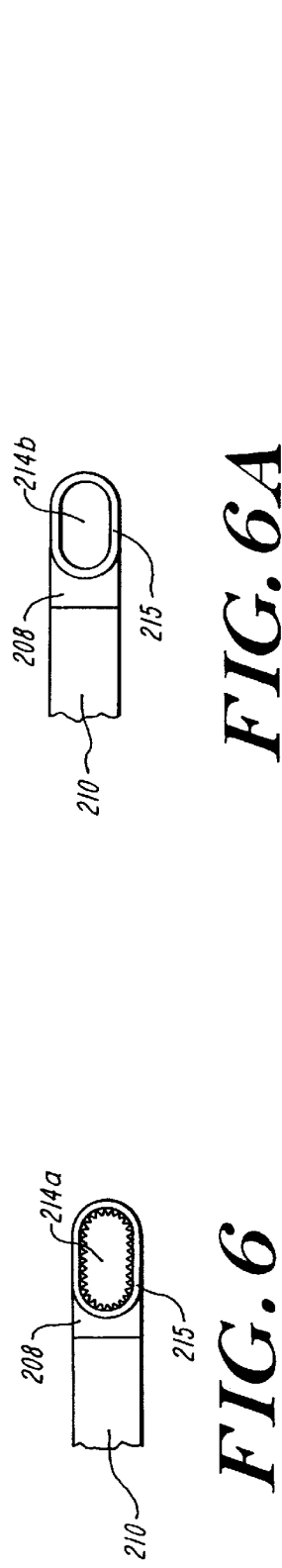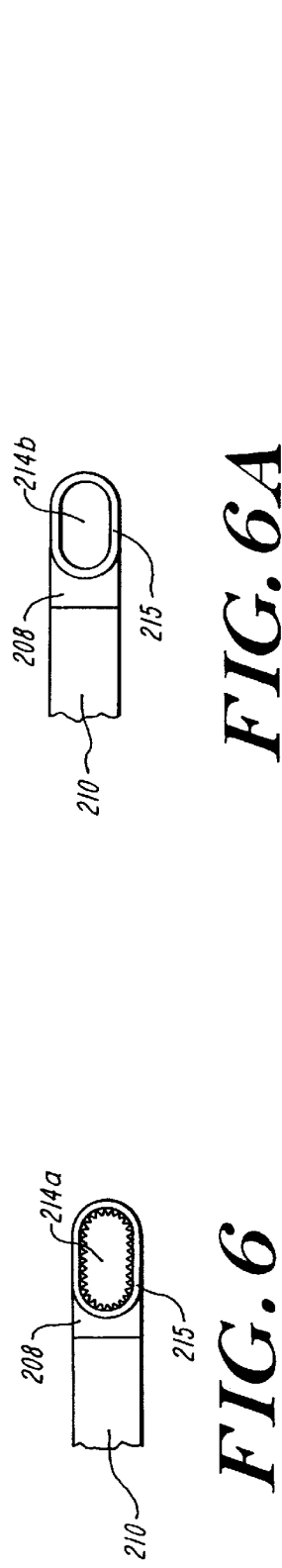

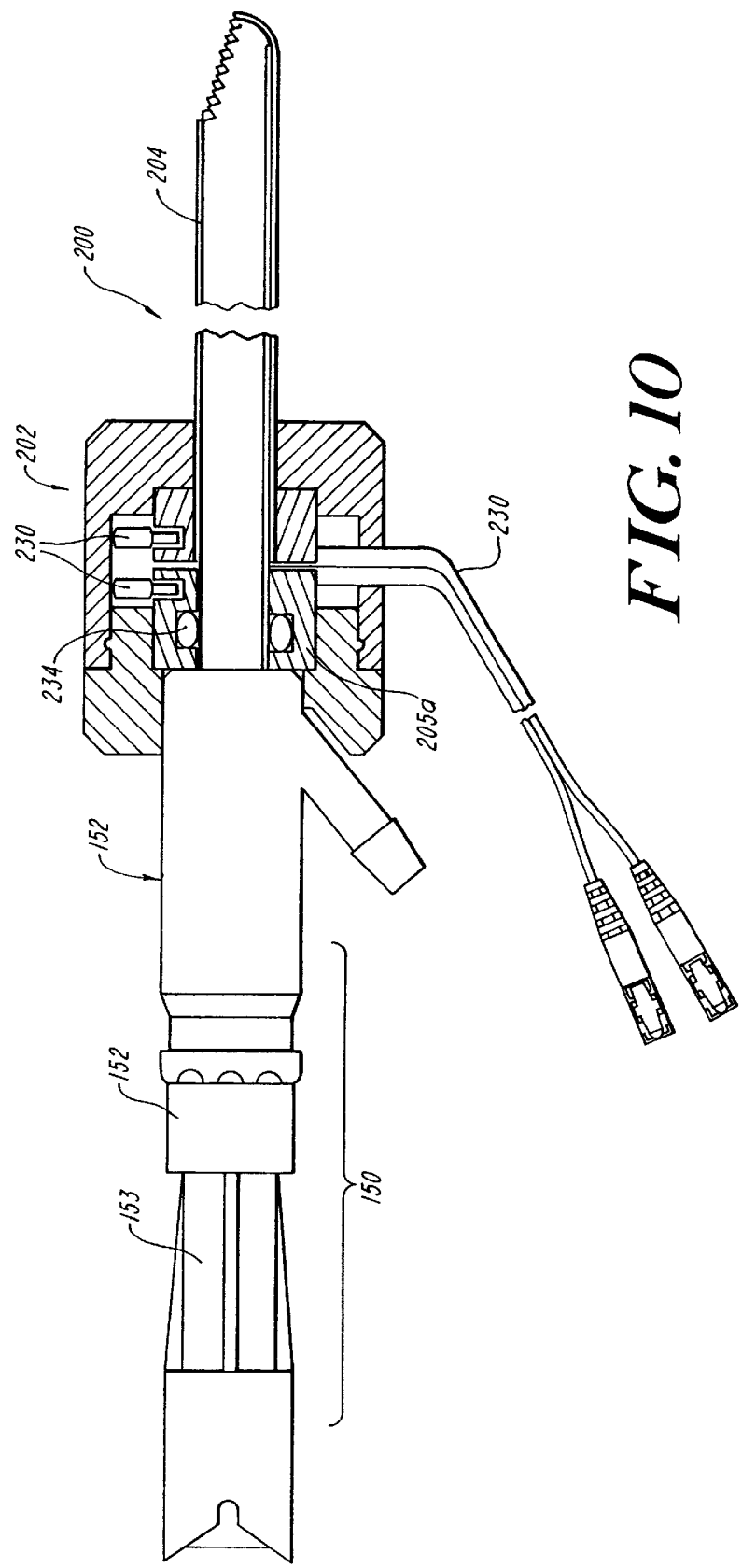

DEVICE FOR CONVERTING A MECHANICAL CUTTING DEVICE TO AN ELECTROSURGICAL CUTTING DEVICE

GOVERNMENT RIGHTS

Not applicable.

CROSS REFERENCE TO RELATED APPLICATIONS

Not applicable.

BACKGROUND OF THE INVENTION

Rotating surgical instruments that mechanically cut, shave, abrade and drill hard or soft tissue are well known in the art and have proven, over time, to be quite useful. Such tools can be used in open or closed surgical procedures to remove affected tissue. Typical rotating instruments used in these procedures include surgical drilling instruments, such as bone drills, and other rotating mechanical cutting and shaving devices, such as morcellators and power shavers.

Conventional power shavers include an inner rotatable drive shaft having an abrading element at a distal end. The drive shaft seats within a central lumen of the shaver housing such that the abrading element is exposed at the distal end. The drive shaft couples to a motor which imparts rotary movement to the shaft. The power shaver mechanically cuts or shaves affected tissue by the direct mechanical contact of the abrading element with the tissue.

One drawback of such devices is that the abrading edge of the instrument must be extremely sharp to enable effective mechanical cutting of the tissue. During the course of the surgical procedure, however, the abrading or cutting edge of the rotating tool tends to dull, thereby decreasing the cutting performance of the tool. When this occurs, the cutting tool must be replaced. The need for frequent replacement of the abrading portion of the device increases the overall time necessary to conduct the surgical procedure while concomitantly increasing the cost of delivering the medical services and in stocking the replacement components for the medical device.

There thus exists a need in the art for rotary surgical devices that are able to provide effective cutting and abrading of tissue while minimizing or eliminating the need to replace selected components, such as the abrading element, of the device. In particular, it would be useful to provide an adapter device to convert such mechanical surgical tools to electrosurgical tools.

The use of mechanical surgical devices can sometimes lead to undesirable bleeding, which must often be controlled using a separate device. It would also be useful to provide a device that enables a mechanical surgical tool to be used in a manner that it can provide a hemostasis effect.

SUMMARY OF THE INVENTION

The present invention pertains to an electrosurgical adapter assembly to convert a mechanical apparatus that includes a rotary, tissue affecting device in the form of one or more rotating blades, a rotating drill, or a rotating shaving/abrading device, so that its tissue-cutting end serves as one electrode of a bipolar electrosurgical tool. The bipolar electrode action effectively cuts tissue at the surgical site without relying solely upon the mechanical cutting action of the tissue affecting device. The rotary surgical device can be in a form such that it is suitable for use in open or closed surgery. The term "closed surgery" is intended to include arthroscopic, endoscopic, hysteroscopic, laparoscopic, and resectoscopic surgical techniques. Closed surgical techniques typically utilize elongated instruments which are inserted into the patient's body through a small incision or a natural orifice, to allow a secondary instrument easy access to the surgical site. A variety of such surgical devices are well known in the art and are well described in the patent literature. Representative devices are described in U.S. Pat. No. 4,842,578 (Johnson et al.), U.S. Pat. No. 5,411,514 (Fucci et al.) and U.S. Pat. No. 5,492,527 (Glowa et al.).

In its basic configuration, the electrosurgical adapter device of the present invention attaches to a rotating, tissue affecting device having a distal, tissue contacting end which serves as an active, mechanically-operated implement for cutting tissue, and provides a mounting block and a sheath extension assembly which are operative to interconnect a pair of electrosurgical energy contacts or leads to energize, on the one hand, the mechanical cutting tool, and on the other hand, an electrode band which is included in the sheath extension and positioned proximal to or surrounding an exposed region of the distal end of the cutting tool. The actual shape and structure of the mechanical cutting device will depend upon the purpose for which the device is to be used. For example, rotating cutting devices and arthroscopic shaving devices are well known in the art and the structure of such devices can be assumed. The rotating, tissue affecting device also includes a proximal end, usually in the form of an elongate drive shaft, which fits within an outer cannula. The cannula and drive shaft typically form co-acting portions of the cutter, and may constitute a disposable assembly. The cannula can form part of an arthroscope, endoscope, hysteroscope, laparoscope, or resectoscope surgical tool as is well known in the art. The adapter device has a shape corresponding to the cannula/cutter shape of the basic mechanical surgical tool.

The adapter includes electrical contacts that electrically connect at one end to outputs of a remote electrosurgical generator and at their other end connect, respectively, to a conductive body portion of the tissue affecting device, and to an electrode extension carried in the adapter sheath fitted over the outer cannula assembly of the tissue affecting device. The contacts energize the mechanical cutting assembly and thus the distal abrading end by transferring cutting energy from the electrosurgical generator to the drive shaft or cannula, on the one hand, and to a distal electrode which is maintained electrically insulated therefrom and is exposed for a small area proximal to or surrounding the cutter at the distal end.

The adapter of the present invention thus converts a simple mechanical tissue cutting device to a bipolar electrosurgical device, or may be used to convert a monopolar electrosurgical device to bipolar operation. When applied to a simple mechanical cutting device, bipolar operation is achieved between the distal end of the rotating, tissue affecting device and/or its surrounding cannula which serves as one energy delivering electrode, and a second electrode carried in an insulating sheath that fits over the cannula. When applied to adapt a monopolar cutting device to bipolar operation, the adapter adds a second electrode carried in an insulating sheath that insulates the electrode from the cannula and positions it so a current path is formed through tissue in a band surrounding an exposed region at the distal end of the cannula.

During closed surgical procedures it is sometimes necessary to supply a fluid to a surgical site in order to distend the surgical area and to improve visibility for the surgeon. The present system converts cutting tools to bipolar electrosurgical operation, allowing use of an isotonic solution (e.g., saline or Ringer's solution) to distend the surgical site, rather than a non-ionic solution. The patient, therefore, is not exposed to potentially dangerous electrolytic imbalances associated with absorption of non-ionic solution into the patient's bloodstream, and the localization of current paths at the cutting locus prevents the ionic solution from degrading the electrosurgical current paths.

A preferred adapter construction readily configured to convert diverse mechanical cutting instruments includes a mounting block that is adapted to mount to the instrument, for example with a sliding bushing or clamp that connects over the existing cannula and establishes electrical connection to the instrument body. An insulated sheath is carried by the mounting block and extends over the cannula to provide an electrical barrier. The sheath contains a further conductor, which may be a conductive layer extending in or on the sheath, that is exposed at its distal end to form a second electrosurgical electrode for defining current paths in a small region of tissue at the cutting end of the tool. Preferably, the mounting block holds an RF plug, socket, or cable to which the electrosurgical energy source is applied, and connects the two outputs to the instrument body and the further conductor, respectively. The sheath and block form a single unit that fits over the existing cannula, insulating the assembly without substantially increasing the diameter of its shaft.

BRIEF DESCRIPTION OF THE DRAWINGS

The invention may be more fully understood from the following detailed description in combination with the drawings in which:

FIG. 1 is a top view of an adapter device for converting a mechanical cutting device to an electrosurgical cutting device;

FIG. 2 is a cross-section front view of the adapter device of FIG. 1.

FIG. 2A is an enlarged view of the proximal portion of the adapter device shown in FIG. 2;

FIG. 3 is an enlarged view of portion A of a distal end of the adapter device of FIG. 1;

FIG. 3A is an enlarged view of an alternative construction of a distal portion of the adapter device;

FIG. 3B is an enlarged view of another alternative construction of a distal portion of the adapter device;

FIG. 4 is a cross-sectional view taken along lines 4—4 of FIG. 1;

FIG. 5 is a front view of an alternative embodiment of the adapter device of the present invention mounted upon a mechanical surgical shaver tool;

FIG. 6 is an enlarged top view of the distal end of the adapter device of FIG. 5;

FIG. 6A is an enlarged bottom view of the distal end of the adapter device shown in FIG. 5;

FIG. 9 is a block diagram of an adapter device coupled to an electrosurgical generator through an impedance transformer; and FIG. 10 is a sectional view of another embodiment of the adapter device of the present invention having a fixed cord assembly and spring contact mounted on a mechanical shaver device.

DETAILED DESCRIPTION OF THE INVENTION

Figure 7:
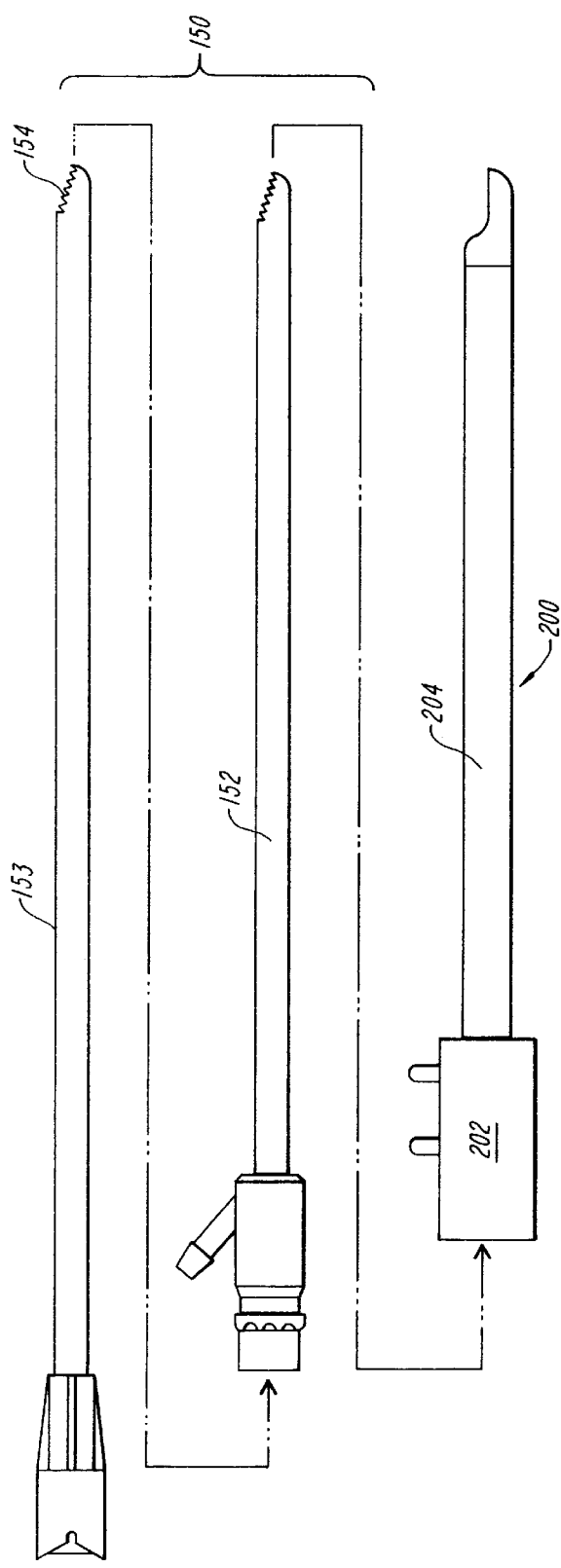
FIG. 7 is an exploded view of the adapter device of FIG. 1 and mechanical shaver device.

The adapter device of the present invention is an electrical connecting and electrode-forming adapter that attaches to an existing surgical tool, such as a purely mechanical, or even a monopolar, shaver or morcellator, and converts it to bipolar electrosurgical operation. As such, it allows the use of isotonic inflation or irrigation fluids for endoscopic electrosurgical procedures, and allows the existing tool to operate while performing hemostasis, and also to operate with increased tool lifetime, or greater effectiveness that may be realized, for example, by electrosurgical treatment of tissue at the cutting or shaving region.

According to the present invention, illustrated in FIGS. 1–10, there is provided an adapter assembly that converts a mechanical surgical tool, e.g., a cutting or shaving device, to a bipolar electrosurgical device. For purposes of illustration the adapter device is described with reference to use with an endoscopic shaving device, but it is understood that the adapter may be used with other endoscopic surgical instruments that perform functions other than shaving of tissue.

Referring now to FIGS. 1–4, in which like elements are provided having like reference designations throughout the several views, an adapter device or sheath 200 includes a mounting region mounting block 202 which, in an exemplary embodiment, may be provided as a plastic block having a first end 202a, with metal bushing 205a disposed therein, and a second end 202b with a metal bushing 205b disposed therein. A bore extends from the first end 202a to the second end 202b of the block 202. The first end 202a of the mounting block 202 may include an alignment mechanism such as a key 203 which provides a means for mechanically aligning and coupling the adapter device 200 with a compatible surgical tool, such as an endoscopic cutting device or shaver. The key 203 is here provided as an alignment notch or opening in the mounting block 202 but it should be understood that the key 203 may alternatively be provided as a pin or other member (e.g., a boss) projecting from a surface of the mounting block 202. The bushing 205a provides an electrical signal path having a relatively low impedance characteristic between the surgical tool and a first pin 224. The bushing 205b provides an electrical signal path having a relatively low impedance characteristic between a conductive portion of the sheath body 204 and a second pin 223.

Alternatively, the relatively low impedance signal path between the adapter device 200 and the surgical tool 150 may also be provided from a side-loaded spring 234 which is compressed by coupling the sheath 200 to a surgical tool 150, for example, and forcing the spring to contact conductive regions of both the bushing 205a and the surgical tool, as shown in FIG. 10. Alternatively, still, a wide variety of means including, but not limited to, brushes and bushings, can be used to provide the desired electrical contact.

It should be noted that although the mounting block 202 is here provided as a plastic member, other adapter devices 200 may be provided having other types of mounting blocks 202. The mounting region is preferably provided as a high quality, reliable, relatively low cost mounting structure which allows the adapter device 200 to be firmly and accurately affixed to the surgical tool in a rapid and relatively simple manner to provide or facilitate an electrical connection between the surgical tool and the adapter device 200. The particular type of mounting block 202 used in any particular application is selected in accordance with a variety of factors including, but not limited to, compatibility with the particular surgical tool to which the adapter device 200 is to be coupled, ease of coupling the mounting block to the surgical tool, ease of manufacture of the particular type of mounting block, cost of manufacture of the mounting block including the cost of the mounting block 202 relative to the cost of the entire adapter device 200, and ease of assembly of the mounting block and sheath body (in the event the mounting block and sheath body are manufactured as separate pieces).

The adapter device 200 further includes a sheath body 204 which is carried by and projects distally from the mounting block 202. The sheath body 204 has a first or proximal end 204a which extends at least part way into the bore of the mounting block 202 and is secured within the mounting block 202 using any suitable fastening technique known to those of ordinary skill in the art. A second portion of the sheath 204, including a second or distal end 204b, projects distally away from the mounting block 202, and preferably extends at least as far as the windowed cutting aperture of the tool to which the assembly attaches.

FIG. 4 illustrates an exemplary configuration of sheath body 204. As illustrated, the innermost layer is a first, nonconductive substrate 212 having a thickness (T1) that is in the range of about 0.15 mm to 0.8 mm. A conductive layer 208 is disposed immediately adjacent an outer surface of the nonconductive substrate 212. Conductive layer 208 can be formed on the outer surface of nonconductive substrate 212 by techniques such as coating, plating, or bonding. The thickness (T2) of conductive layer 208 is in the range of about 0.02 to 0.15 mm. An insulative layer 210 is disposed immediately adjacent the outer surface of the conductive layer 208. The thickness (T3) of the insulative layer 210 is in the range of about 0.025 mm to 0.1 mm. The nonconductive substrate 212 defines a substantially circular opening 206 in the sheath 204 within which a portion of the endoscopic surgical tool 150 such as the outer cannula 152, as shown in FIG. 7, may be disposed.

One of ordinary skill in the art will appreciate that the various layers that make up the sheath body 204 can be made from a variety of suitable materials. The nonconductive substrate 212, for example, is to be made from a material which is biocompatible and which has good dielectric properties, sufficient to provide a nonconductive barrier between the conductive portion of the sheath and the outer cannula of the device. In addition, the substrate 212 should be made from a material with sufficient strength and manufacturing tolerances to allow the sheath body 204 to accept a portion of a surgical tool without an interference fit or excessive tightness. Exemplary materials include, but are not limited to, polymers such as polycarbonate, polyvinyl chloride, and polysulfones.

The conductive layer 208 should likewise be a biocompatible material that is able to be adhered to substrate 212. Exemplary materials may be gold, silver and stainless steel, although a lesser conductive material may be used in buried or coated regions, with only exposed regions being formed of such biocompatible metal. Further, the conductive layer 208 can be formed from conductive paints and inks.

The insulative layer 210 should be formed from a biocompatible material that provides good dielectric properties so as to provide electrical insulation. One of ordinary skill in the art can readily ascertain suitable materials for insulative layer 210. Exemplary materials include polyester shrink tubing and Kynar coatings.

The particular materials and techniques for manufacturing each of the layers 208, 210 and 212 of sheath body 204 are selected in part such that tolerances can be controlled to provide a snug fit of the surgical device within the sheath 204. This mininizes the overall diameter of the assembled device.

Referring again to each of the several views, and in particular to FIG. 2, a connecting assembly 222 projects from the mounting block 202 and provides an electrical signal path from a power source such as an electrosurgical generator to the conductive layer 208 of the sheath body 204 and to a conductive portion of the tissue affecting device. In the illustrated embodiment, the connecting assembly 222 includes a pair of connecting pins 223, 224 disposed through the mounting block 202. The first pin 224 makes an electrical contact to the conductive bushing 205a. The second pin 223 has a surface in electrical contact with the conductive layer 208 of sheath body 204 via bushing 205b and thus provides an electrical signal path to the conductive layer 208. This configuration enables the entire assembly to mount on a standard surgical tool, such as an endoscopic shaver, so that its cutting assembly is energized with an RF output via pin 224 and bushing 205a while an exposed conductive area of the sheath forms the second electrode and is connected to the second generator output via pin 223, bushing 205b, and conductive layer 208.

It should be appreciated that alternatively the connecting assembly 222 may be replaced by a fixed cord assembly 230 (see FIG. 10) thus allowing the adapter device 200 to be efficiently manufactured, and eliminating one field assembly step.

As shown in FIGS. 2–4, the conductive layer 208 extends along the length of the sheath, and is exposed for a distance L (FIG. 3) proximally from the furthermost edge of distal end 204b of sheath 204. The distance L is typically in the range of about 10 mm to 15 mm. The remaining portions of the outer surface of the sheath body 204 are covered by the nonconductive material 210. The conductive portion 208 extends proximally beyond a second end of the aperture 214 by a distance L1 which is typically in the range of about 1 mm to 4 mm. The exposed electrode area may extend for a greater length without impairing its operation, and a larger exposed conductive layer 208 may be desirable for ease of manufacturing. However, in general a band extending for about one to four times (and preferably about three times) the width of non-conductive region 215 is appropriate to achieve effective hemostasis.

In operation, when the adapter device 200 is disposed over a mechanical surgical tool, such as a shaver, the cutting portion 154 of the surgical tool 150 is exposed through the aperture 214 and its tool is energized via the proximal end signal connector pin 224. Thus, RF current effective for coagulation or local hemostasis flows in a region at the moving tool end through a small region of tissue extending near the entire non-conductive region 215 when the leads or pins 223, 224 are energized. Thus, when the cutting portion moves with either rotational or translational movement, the movement of the cutting tool tip proximate the exposed conductive region 208 at the distal end 204b of sheath body 204 effectively results in mechanical cutting proceeding simultaneously with local hemostasis.

The conductive layer 208 provides a conductive path to the second active electrode signal pin 223 which is electrically coupled to an electrosurgical generator. In this manner, bulk hemostasis takes place about the entire periphery of the cutting area defined by the aperture 214. The ability to provide bulk hemostasis in the cutting area during movement of the cutting device (for example, movement of a blade in a rotational or nibbling movement) in combination with the close physical proximity of conductive layer 208 to the conductive portion of the cutting element effectively provides tissue sealing limited to the localized region of cutting.

By providing a system in which the hemostasis takes place in the cutting area, it is not necessary for the operator to stop using the cutting device to provide the hemostasis function. Thus, the adapter assembly 200 provides a separately-mountable RF connector and electrode set that converts a mechanical cutting device into an electrosurgical cutting device to simultaneously provide hemostasis in conjunction with its function of cutting, shaving, or otherwise affecting tissue. As shown in FIG. 3, the distal end 204b of sheath body 204 includes the aperture 214 which is defined by a nonconductive perimeter band 215. The size and shape of the aperture 214 is selected to allow proper operation of the cutting device exposed in the aperture. Thus, while the aperture 214 is here shown having an oval shape with a major axis typically of about 10 mm and a minor axis typically of about 5 mm, it should be appreciated that in other embodiments it may be desirable to provide aperture 214 having other sizes and shapes including but not limited to a square shape, a rectangular shape, a triangular shape, or an irregular shape. The particular size and shape of aperture 214 is typically selected to accommodate the size and shape of a particular cutting device and may be positioned asymmetrically about the cutting opening. It should be noted that to accommodate a cutting device, the aperture 214 need not have the same shape as the cutting device. In general, the shape may also depend upon the firmness of the tissue to which the cutting tool is directed, with the aperture being sized to allow a sufficient, but not excessive, amount of tissue to enter the cutting path of the tool moving internally within the aperture.

The nonconductive area 215 can be provided by a masking step during conductor fabrication, or by removing or otherwise preventing the conductive layer 208 from covering the sheath body substrate 212 in a predetermined region corresponding to the desired non-conductive area. Here, the nonconductive perimeter area 215 is provided having an oval shape. It may further be a beveled surface, or have such a step or relief as may be appropriate for achieving the desired rake angle and tissue entry penetration for effective operation of the moving cutter blade inside.

Figure 8:
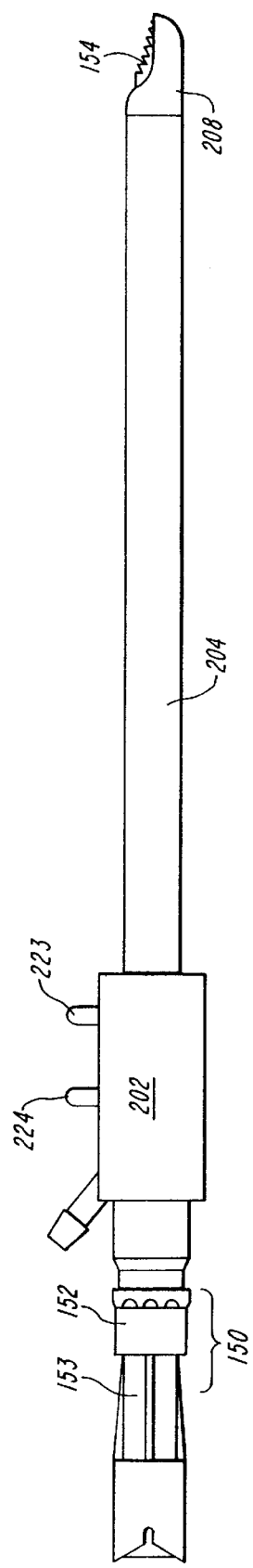
FIG. 8 is an assembled front view of the device of FIG. 7.

The width of the area 215 is selected to prevent an excitation voltage signal provided by the electrosurgical RF signal generator from short circuiting between conductive region 208 and the cutting tool assembly. It is preferable to provide the band 215 having the minimum width possible while still being able to maintain electrical insulation at the applied excitation voltage. By keeping the width of the band of insulating material small, surrounding tissue is better able to maintain firm physical contact against the conductive electrode area 208 to provide dependable electrical contact. In one embodiment, for operation with an electrosurgical generator setting of up to about 70 watts (W), the band 215 is provided having a width typically of about 0.8 mm. FIG. 8 illustrates the adapter assembly of the present invention affixed to a mechanical shaver or other tissue-affecting device 150. As shown, the mounting block 202 provides a connection for the signal source, and positions the exposed electrode 208 at the aperture 214 about the cutter 154 which has been energized at the proximal end by the electrode connection 223 of the mounting block.

In operation, the hemostasis takes place at the cutting area and thus it is not necessary to cease cutting in order to provide hemostasis. Thus, with the present invention one can provide hemostasis in conjunction with cutting simultaneously. If bleeding nonetheless occurs, the operator may suspend the mechanical cutting while maintaining the electrosurgical energy. Since no repositioning of the cutter is needed, such operation is quick, accurate, and does not disrupt the direction or area of cutting. Thus, the provision of a conductive electrode region 208 closely surrounding the entire cutting aperture assures effective coagulation during routine operation and facilitates continuity of the cutting procedure. The exposed electrode area 208 may be positioned quite close to the cutting tool and be limited in overall surface area to assure that bulk hemostasis takes place all along the periphery of the cutting area.

The foregoing embodiment may be fabricated using a sheath body 204 formed of a polycarbonate substrate having appropriate coatings disposed thereon. In another embodiment the sheath body 204 may be fabricated of stainless steel tubing, a so-called hypotube, which then has an insulative coating disposed over the internal surfaces thereof and over selected portions of external surfaces thereof. The assembly may even be fabricated integrally with the cannula of a replaceable cannula/cutter assembly, in which case it would preferably be supplied as a kit complete with matched cutting tool. As one of ordinary skill in the art will appreciate, the hypotube may be an annealed stainless steel so as to be useful with bendable shaver devices.

FIGS. 3A and 3B illustrate alternative configurations for the distal portion 204b of sheath body 204, in which elements corresponding to like elements in FIGS. 1–4 are provided having like reference designations. With particular reference to FIG. 3A, the distal portion 204b of sheath body 204 includes the aperture 214 and the conductive region 208. In this particular embodiment, the conductor extends ahead of the aperture over a distance L3 to the distal extremity of the sheath 204 and the conductive portion 208 surrounds all sides of the aperture 214. The conductive portion 208 also extends before the aperture 214 along a length L4.

FIG. 3B illustrates another configuration for the distal portion 204b of sheath body 204. In FIG. 3B, the distal portion 204b of sheath body 204 includes the aperture 214 and the conductive region 208. In this particular embodiment, the distal end of sheath 204 is provided having a square or rectangular shape. The conductive portion 208 is disposed around the aperture 214, outside of the non-conductive band 215.

With reference to FIGS. 3–3B, the overall length of aperture 214 is generally in the range of about 5–10 mm. The dimension (L1 and L4) by which the conductive portion 208 extends proximally from non-conductive region 215 is about 1 to 4 mm. In the embodiment of FIG. 3A, the length (L3) is about 1 to 4 mm.

A further embodiment of adapter device 200, which is useful to extend the achievable hemostatic control, is described below with reference to FIGS. 5–6A, in which elements corresponding to like elements in FIGS. 1–4 are provided having like reference designations. With particular reference to FIG. 5, the distal portion 204b is shaped to provide a pair of apertures 214a, 214b. When the sheath body 204 is mounted on its cutting tool, a blade may cut tissue through one of the apertures 214a while the other aperture 214b is configured to provide hemostasis only. This second aperture 214b is provided with an electrode structure that does not rely on the cutting blade as its electrode, and thus provides a high level of hemostasis that does not vary with blade position when the cutter is stopped. For example, aperture 214b may extend through the sheath to expose a solid, non-apertured, region of the underlying conductive cannula 152, so that the cannula surface, rather than a cutting blade, acts as the second electrode surface.

As can be clearly seen in FIGS. 6 and 6A, the conductive portion 208 provides a conductive electrode disposed around each of the apertures 214a, 214b. Thus, hemostasis is provided in each of the areas defined by apertures 214a, 214b. It should be noted that although the apertures 214a, 214b are here shown located in a particular portion of the sheath at the distal end of the cutting device and having an oval shape, it should be appreciated that the apertures and distal end 204b of the sheath 204 may be provided having a variety of shapes and may be located in a variety of different locations including any of the locations described above in conjunction with FIGS. 3–3B. Advantageously, however, in this embodiment the hemostasis aperture 214b is aligned opposite the cutting aperture, and thus may be conveniently positioned on the exact site being cut by operator with the cutting/hemostasis tool aperture 214a, by performing a simple axial rotation around the shaft axis of the device, without otherwise shifting the cutting position, realigning or withdrawing the implement. The second electroded aperture thus provides the benefits of a separate electrosurgical sealing tool without the positioning drawbacks that would be introduced by a separate hemostasis instrument.

FIGS. 7 and 8 illustrate the relationship of the adapter device 200 of the present invention to a conventional mechanical surgical tool 150. As illustrated, the adapter 200 has a mounting block 202 and a distally extending sheath body 204.

For purposes of illustration the mechanical surgical tool 150 is an endoscopic shaver device having an outer cannula 152 within which is mounted an inner, tissue-affecting element 153. The tissue-affecting element 153 may be rotatable or translatable such that a distal, cutting portion 154 thereof is able to cut or abrade tissue. The distal end of the outer cannula 152 has an aperture through which at least part of the cutting portion 154 may project.

The mechanical cutting tool is assembled by placing the tissue-affecting element 153 within the outer cannula 152. This tool 150 may be converted to a bipolar surgical tool by sliding the adapter device 200 over outer cannula 152.

Referring now to FIG. 9, an adapter device 250 for converting a mechanical cutting device to an electrosurgical cutting device is coupled to a first port of an impedance transformer 252. The adapter device 250 may be similar to the adapter device 200 described above. A second port of the impedance transformer 252 is coupled to an output port of an electrosurgical generator 254, e.g., to the bipolar output port of the generator.

In operation, the electrosurgical generator 254 provides a drive signal having a predetermined or controlled signal energy to a signal port having a predetermined impedance characteristic. For example, a typical electrosurgical generator may provide a bipolar output with power settings of between twenty and one hundred watts, and provide a voltage-limited signal or otherwise control the signal energy at the port to achieve the selected power delivery. While these generators work well with many bipolar devices, the adapter of the present invention presents a novel situation in which a sheath presents an electrode 208 that is positioned in proximity to, but curving sharply away from, a second electrode which has been defined by the pre-existing cutting tool and aperture of the device on which the adapter 250 is fitted. Such pre-existing cutting tool has dimensions determined by purely mechanical considerations, without reference to operation as an electrode. Thus, the standard output of the generator 254 may be poorly adapted to effectively transfer power to tissue near the cutting tool. The drive voltage may be excessive, leading to arcing or charring near the tool, and causing irregular current flow and heat distribution in the target tissue. To provide an efficient energy transfer between the signal port of the electrosurgical generator 254 and the adapter device 250, the adapter device 250 would ideally be provided having a predetermined impedance characteristic selected to maximize the efficiency of the power or energy transfer. In practice, however, the adapter device 250 has exposed electrodes of small size, and may operate with a particular instrument, or to cut a specific tissue having its own characteristic conduction properties. The adapter device 250 therefore typically has an impedance characteristic which would not result in an efficient application of the energy from the electrosurgical generator 254 to the tissue path contacted by the electrodes formed with the adapter device 250.

Thus, in accordance with this aspect of the invention, the impedance transformer 252 is configured with input and output sides that are impedance-matched to the generator 254 and to the adapter 250, respectively. Transformer 252 has a first port having an impedance characteristic selected to provide an efficient power transfer from the electrosurgical generator 254 and a second port having an impedance characteristic which is selected to provide an efficient power transfer to the adapter device 250. For example, the transformer may be configured to produce an output voltage across the tissue electrodes, that is high enough to drive the applied power across the tissue in contact therewith but is below a breakdown or charring level. For example, where the sheath is to deliver up to seventy watts of power, the transformer 252 may be wound to match the respective generator and adapter/tissue impedances while reducing the voltage appearing at the generator port by a factor of about two, to a level which heats tissue more effectively and controllably. For other instrument diameters, aperture size and tool configurations, proper matching may involve increasing the voltage. In this way, a controlled and predetermined amount of signal power as indicated or measured by the electrosurgical generator 254 is effectively transferred from the signal generator 254 to and applied by the adapter device 250.

Although the impedance transformer 252 is here shown as a piece separate from the adapter device 250, it is to be understood that in some embodiments, the transformer 252 may advantageously be provided as an integral component or subassembly of the adapter device 250 or the generator 254.

FIG. 10 illustrates yet another embodiment of the adapter of the present invention. In this embodiment a fixed power cord assembly 230 attaches to the mounting block 202. As further shown in that FIG. a flex spring 234 or conductive elastic seal ring 234 acts as a contact to interconnect one side of the power source directly to the conductive cannula of the 10 mechanical tool via a bushing or collar similar to bushing 205a of FIG. 1.

The foregoing electrosurgical tissue cutting devices and sheaths are adapted for use in surgical procedures including, but not limited to, arthroscopic, endoscopic, hysteroscopic, laparoscopic, or resectoscopic surgical procedures.

Having described preferred embodiments of the invention, it will now become apparent to one of ordinary skill in the art that other embodiments incorporating the concepts herein disclosed may be used. It is felt, therefore, that these concepts should not be limited to disclosed embodiments but rather should be limited only by the spirit and scope of the appended claims. The contents of all cited references are expressly incorporated herein in their entirety.

What is claimed is:

1. An adapter device for a mechanical cutting device, the adapter device comprising:
 a mounting block adapted to couple the adapter device to the mechanical cutting device;
 an electrical connecting element coupled to said mounting block;
 a sheath carried by said mounting block and coupled to said connecting element, said connecting element providing a conductive pathway between said sheath and the mechanical cutting device, said sheath having an inner surface which defines a passageway adapted to accept the mechanical cutting device, and at least a portion of said sheath which corresponds to the inner surface of said sheath including a non-conductive substrate and a first conductive layer disposed over the substrate with an insulating layer disposed over the conductive layer, wherein said sheath has a proximal portion having an open end and a distal portion having an aperture positioned by the sheath at a cutting tool of the mechanical cutting device, the aperture being defined by a band of the non-conductive substrate closely separating a conductive portion of the mechanical cutting device from an exposed portion of the conductive layer such that upon coupling of the sheath to the mechanical cutting device and powering the mechanical cutting device, the conductive layer provides an electrical return at the distal portion of the sheath to the connecting element such that the adapter device converts the mechanical cutting device for bipolar electrosurgical operation at the aperture.

2. The adapter device of claim 1 wherein said connecting element comprises first and second electrodes with a first one of said first and second electrodes coupled to said mounting block and a second one of said first and second electrodes coupled to the conductive layer of said sheath.

3. The adapter device of claim 2 wherein the aperture defines a cutting area and the conductive layer is exposed about the aperture proximate the cutting area.

4. The adapter device of claim 1, wherein said sheath is a flexible sheath assembly.

5. The adapter device of claim 1, wherein the device is configured for a mechanical cutting instrument having a removable and replaceable cannula, and said mounting block and sheath are permanently affixed to the cannula to form an electrosurgical replacement cutter tool assembly.

6. The adapter device of claim 1, wherein the sheath further comprises a second aperture positioned to expose a region of the mechanical cutting device and form a bipolar electrode arrangement for contacting and hemostatic sealing of cut tissue.

7. A method of converting a mechanical cutting device having a cutting blade, such method comprising the steps of:
 providing a sheath with an open proximal end and a distal end having an apertured cutting area, the sheath including a non-conductive substrate, a conductive layer and an insulating layer;
 placing a plurality of conductive elements to provide a conductive pathway to the sheath and to the cutting device;
 coupling the cutting device to the sheath by inserting the cutting device through the open proximal end such that the cutting device is aligned at the apertured cutting area and is separated from an exposed portion of the conductive layer by a band of said non-conductive substrate at the cutting area;
 such that by connecting an electrosurgical generator to at least one of the plurality of conductive elements and activating the electrosurgical generator, the cutting device operates as a bipolar electrosurgical instrument.

8. The method of claim 7, wherein the first conductive element and the second conductive element are each metal pin connectors.

9. The method of claim 7, wherein the first conductive element and the second conductive element are formed by a cord assembly.

10. An adapter device for converting a mechanical or monopolar cutting instrument, wherein the mechanical or monopolar cutting instrument includes a handle, a cannula and a cutting blade that moves within a cutting aperture of the cannula to effect tissue cutting, said adapter device comprising
 a mounting block
 an insulative sheath assembly carried by and extending from the mounting block and carrying an enclosed conductor extending along the length of the sheath to a window and with an exposed conductive portion of said conductor at said window, and
 an electrosurgical connector carried by said mounting block for connecting an electrosurgical energy source to said enclosed conductor and to said mechanical or monopolar cutting instrument,
 said mounting block and sheath being configured for insertion of the cannula therein such that said exposed conductive portion is positioned and aligned adjacent the cutting aperture and is spaced from a conductive portion of the cutting instrument by a band of insulation to effectively provide bipolar electrosurgical electrodes at the window, thereby converting the mechanical or monopolar cutting instrument to a bipolar device.

11. An adapter assembly configured to attach to a monopolar or mechanical cutting device, the adapter assembly comprising:
 a generally tubular non-conductive substrate having an inner surface and an outer surface;
 a conductor disposed over the outer surface of the substrate;
 an insulating layer disposed over the conductor
  wherein a distal portion of the substrate includes an opening formed therein in a side of the tubular substrate which defines a cutting area, at least a partial perimeter of the cutting area being defined by a band of the non-conductive substrate closely separating an exposed region of the conductor from the opening, a proximal portion of the substrate having an open end adapted for insertion of the monopolar or mechanical cutting device therein, and having plurality of conductive elements for providing a conductive pathway between the conductor and the cutting device; and such that when the substrate is fitted over the cutting device and an electrosurgical generator is connected to at least one of the plurality of conductive elements, the conductor provides an electrical return at the distal portion of the sheath to an active electrode such that the device is converted to operate as a bipolar device.

12. The adapter assembly of claim 11, wherein the plurality of conductive elements includes:

a first conductive element adapted for connection to the conductor and to the electrosurgical generator; and a second conductive element adapted for connection to the cutting device and to the electrosurgical generator.

13. The adapter assembly of claim 12, further comprising and alignment feature adapted to align the cutting device within the sheath.

14. The adapter assembly of claim 11, wherein upon coupling of the cutting device to the adapter assembly, a blade within the cutting device is capable of at least one of longitudinal and rotational movement within the sheath.

15. The adapter assembly of claim 11, wherein upon coupling of the cutting device to the adapter assembly, the cutting blade of the cutting device is disposed at the opening of the distal portion of the adapter assembly.

16. The adapter assembly of claim 15, wherein the blade is separated from the conductive layer by no more than about two millimeters.

17. The adapter assembly of claim 11, wherein the opening extends for between about five to about fifteen millimeters of a longitudinal length of the sheath.

18. The adapter assembly of claim 11, wherein the distal portion of the adapter assembly has an end distal to the opening.

19. The adapter assembly of claim 13, wherein the distal end is substantially arcuate.

20. The adapter assembly of claim 13, wherein the distal end is substantially straight.

21. The adapter assembly of claim 11, wherein the exposed conductor is disposed distally and proximally of the opening at the distal portion of the substrate.

22. The adapter assembly of claim 11, wherein upon coupling of the cutting device to the adapter assembly, the cutting device is insulated from the intermediate area and proximal portion of the adapter assembly by insulating material.

23. The adapter assembly of claim 20, wherein the conductor is applied on the non-conductive substrate and the insulating layer is applied on the conductor.

* * * * *